US012198796B2

(12) United States Patent
Hanson et al.

(10) Patent No.: US 12,198,796 B2
(45) Date of Patent: Jan. 14, 2025

(54) PATIENT DATA GUIDED DIETARY ADHERENCE AND DELIVERY

(71) Applicant: ShareSafe Media, LLC, Mobile, AL (US)

(72) Inventors: Robert B. Hanson, Mobile, AL (US); Peter Pronovost, Novelty, OH (US); Barry Sudduth, Central, SC (US)

(*) Notice: Subject to any disclaimer, the term of this patent is extended or adjusted under 35 U.S.C. 154(b) by 315 days.

(21) Appl. No.: 17/564,879

(22) Filed: Dec. 29, 2021

(65) Prior Publication Data
US 2022/0208352 A1 Jun. 30, 2022

Related U.S. Application Data
(60) Provisional application No. 63/131,534, filed on Dec. 29, 2020.

(51) Int. Cl.
G06Q 10/00 (2023.01)
A47J 36/32 (2006.01)
A47J 37/06 (2006.01)
G06F 16/25 (2019.01)
G06Q 10/083 (2023.01)
G16H 20/60 (2018.01)

(52) U.S. Cl.
CPC ............ *G16H 20/60* (2018.01); *A47J 36/321* (2018.08); *A47J 37/0664* (2013.01); *G06F 16/252* (2019.01); *G06Q 10/083* (2013.01)

(58) Field of Classification Search
CPC ..... G16H 20/60; A47J 36/321; A47J 37/0664; G06F 16/252; G06Q 10/083
See application file for complete search history.

(56) References Cited

U.S. PATENT DOCUMENTS

| | | | |
|---|---|---|---|
| 2016/0241660 A1* | 8/2016 | Nhu | H04W 4/80 |
| 2017/0000422 A1* | 1/2017 | Moturu | A61B 5/0022 |
| 2018/0249735 A1* | 9/2018 | Espinosa | G06Q 10/0875 |
| 2018/0308066 A1* | 10/2018 | Hadatsuki | G06Q 10/1095 |
| 2019/0062813 A1* | 2/2019 | Amin | B01L 3/5635 |
| 2021/0241881 A1* | 8/2021 | Avery | G16H 10/60 |
| 2021/0375155 A1* | 12/2021 | Brust | A47J 47/005 |

FOREIGN PATENT DOCUMENTS

WO WO-2022013259 A1 * 1/2022 ......... G06F 21/6254

* cited by examiner

*Primary Examiner* — Rajesh Khattar
(74) *Attorney, Agent, or Firm* — Edward Brinkley Garner, III; James Hunter Adams; AdamsIP, LLC

(57) ABSTRACT

Systems and methods for providing meals include determining a meal plan for an individual, based on health information for the individual. The meal plan includes at least one dietary requirement and at least one dietary restriction. A meal is provided to the individual, in compliance with the at least one dietary requirement and the at least one dietary restriction of the meal plan. A degree of compliance is determined for the individual with respect to the provided meal. The meal plan is revised in accordance with the degree of compliance.

20 Claims, 7 Drawing Sheets

PATIENT DATA GUIDED DIETARY ADHERENCE AND DELIVERY

CROSS REFERENCES TO RELATED APPLICATIONS

This application claims priority to U.S. Provisional Application Ser. No. 63/131,534 filed Dec. 29, 2020, which is incorporated herein in its entirety by reference.

FIELD OF THE DISCLOSURE

The subject matter of the present disclosure refers generally to a system and method for providing a health-oriented diet to a patient, responsive to patient health information and diet compliance information.

BACKGROUND

Poor diet is connected to health problems, including diabetes and cancer, among patients in a variety of demographics. The causes of poor diet can include behavioral factors, but can also include socioeconomic factors, such as food insecurity and food deserts, where healthy food may be economically or geographically difficult to obtain. The health impact of a poor diet is particularly pronounced among older adults. Diet quality, and easy access to healthy food, has a substantial impact on the physical and cognitive condition of individuals, with implications for bone health, eye health, vascular function, the immune system, and a variety of other bodily processes.

Accordingly, there is a need in the art for a system and method for designing meal plans comprised of meals that can be easily prepared within a smart appliance that relays data back to the system so that it can modify the meal plan to increase compliance.

SUMMARY

A system and method for providing food to a user is provided, wherein the food is selected to provide nutritional benefits in accordance with the user's nutritional needs and taste preferences. Generally, the system and method of the present disclosure are designed to generate a meal plan for an individual, and to ensure compliance with that meal plan. Information regarding diet compliance may be collected and may be used to alter the meal plan in accordance with the individual's needs and preferences. In addition, implementations of the present principles provide for tracking of diet compliance by the patient in order to assist a caregiver to tailor subsequent food deliveries and provide foods that the patient finds more palatable. Diet compliance information can also be used to help the caregiver make a decision regarding an intervention, for example if the patient is not eating enough. It is particularly contemplated that the present embodiments may be helpful to aging patients, as aging is often accompanied by a loss of taste and smell that results in reduced appetite due to a decreased interest in food.

In some cases, poor oral health or a decreased ability to swallow can make eating uncomfortable for a patient. Furthermore, some patients have mobility constraints, making it difficult for them to shop for food, lift heavy jars, open containers, and prepare meals for themselves. A patient's location can furthermore pose a difficulty, as even healthy patients may not have a source for healthy food near their homes. Additionally, many people have preventable chronic diseases, which may be related to poor diet and to physical inactivity. These diseases can include, for example, cardiovascular disease, high blood pressure, diabetes, some cancers, and poor bone health. Even in the absence of a clear disease or disorder, vitamin deficiencies can decrease a person's quality of life. Some examples of nutrients and vitamins that may be missing in a person's diet include flavonoids, folate, and carotenoids, which are found in a variety of healthy fruits and vegetables.

The present embodiments may therefore provide medically and nutritionally tailored meal deliveries to individuals. These individuals may include, for example, homebound and critically, or chronically, ill individuals. The delivery of food to such individuals may provide a substantial improvement in the patient's health and overall quality of life. The present embodiments may further provide compliance systems to monitor whether the individuals are following the prescribed diet. Responsive to the compliance information, the present embodiments may automatically tailor future food deliveries to the patient's changing needs.

Compliance with a meal plan may be determined with the use of scannable codes that are applied to the meals prior to delivery. Through the use of, for example, a smart phone application or a smart oven, a patient may scan the scannable code so that the system can confirm that the individual did prepare and/or consume a meal, or part of a meal. The system may also ask the patient questions regarding the meal via the smart phone application and/or a smart oven, which the system may save as patient data. This patient data may be used by the system to determine a user's nutrition, food preferences, and to establish and find alternative foods that the user would prefer, while still meeting dietary requirements.

In particular, systems and methods for providing meals include determining a meal plan for an individual, based on health information for the individual. The meal plan may include at least one dietary requirement and at least one dietary restriction. A meal may be provided to the individual, in compliance with the at least one dietary requirement and the at least one dietary restriction of the meal plan. A degree of compliance may be determined for the individual with respect to the provided meal. The meal plan may be revised in accordance with the degree of compliance.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purpose of the system and method disclosed herein. Those skilled in the pertinent art should also realize that such equivalent designs or modifications do not depart from the scope of the system and method of the present disclosure.

DESCRIPTION OF THE DRAWINGS

These and other features, aspects, and advantages of the present disclosure will become better understood with regard to the following description, appended claims, and accompanying drawings where:

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components. As used herein, the term "created vector" and grammatical equivalents refers to the one or more vectors created by the processor based on the mapped activation levels of the one or more sensors. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Figure 1:
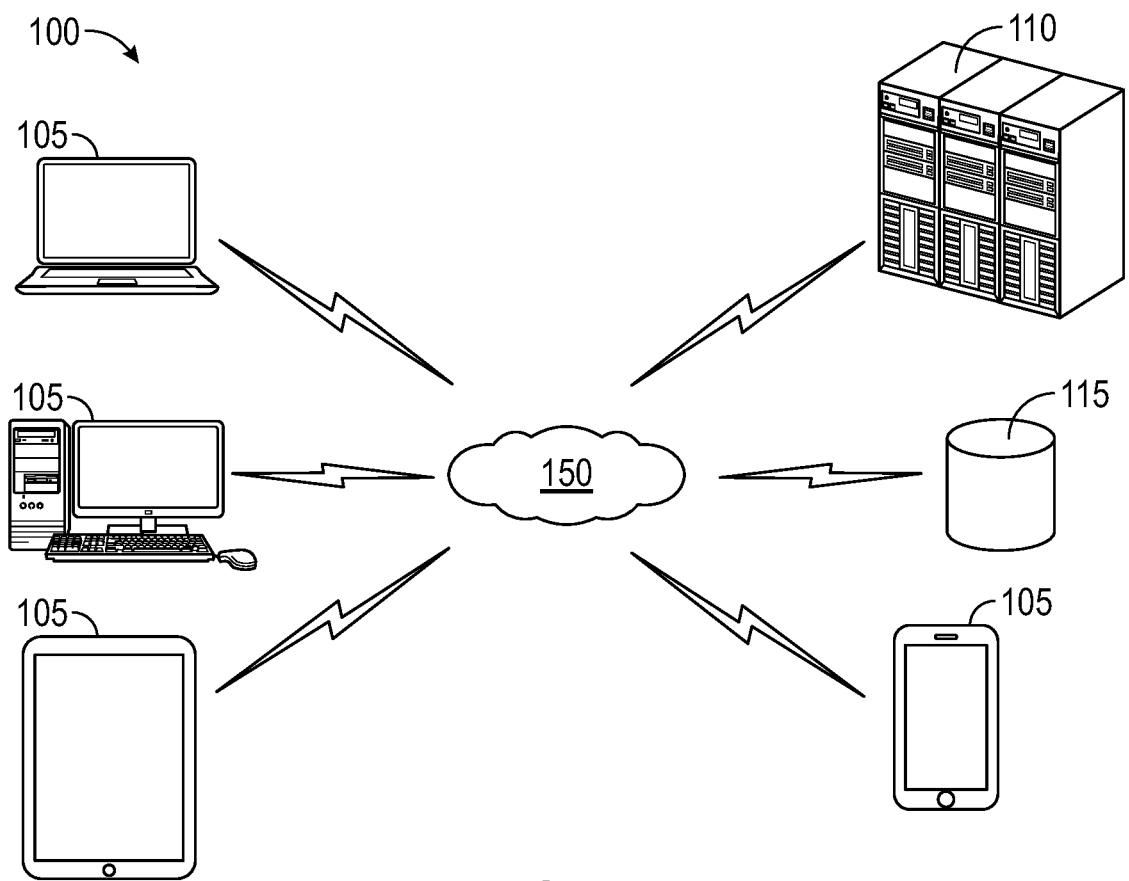
FIG. 1 illustrates a system embodying features consistent with the principles of the present disclosure.

FIG. 1 depicts an exemplary environment 100 of the system 400 consisting of clients 105 connected to a server 110 and/or database 115 via a network 150. Clients 105 are devices of users 405 that may be used to access servers 110 and/or databases 115 through a network 150. A network 150 may comprise of one or more networks of any kind, including, but not limited to, a local area network (LAN), a wide area network (WAN), metropolitan area networks (MAN), a telephone network, such as the Public Switched Telephone Network (PSTN), an intranet, the Internet, a memory device, another type of network, or a combination of networks. In a preferred embodiment, computing entities 200 may act as clients 105 for a user 405. For instance, a client 105 may include a personal computer, a wireless telephone, a streaming device, a "smart" television, a personal digital assistant (PDA), a laptop, a smart phone, a tablet computer, or another type of computation or communication interface 280. Servers 110 may include devices that access, fetch, aggregate, process, search, provide, and/or maintain documents. Although FIG. 1 depicts a preferred embodiment of an environment 100 for the system 400, in other implementations, the environment 100 may contain fewer components, different components, differently arranged components, and/or additional components than those depicted in FIG. 1. Alternatively, or additionally, one or more components of the environment 100 may perform one or more other tasks described as being performed by one or more other components of the environment 100.

As depicted in FIG. 1, one embodiment of the system 400 may comprise a server 110. Although shown as a single server 110 in FIG. 1, a server 110 may, in some implementations, be implemented as multiple devices interlinked together via the network 150, wherein the devices may be distributed over a large geographic area and performing different functions or similar functions. For instance, two or more servers 110 may be implemented to work as a single server 110 performing the same tasks. Alternatively, one server 110 may perform the functions of multiple servers 110. For instance, a single server 110 may perform the tasks of a web server and an indexing server 110. Additionally, it is understood that multiple servers 110 may be used to operably connect the processor 220 to the database 115 and/or other content repositories. The processor 220 may be operably connected to the server 110 via wired or wireless connection. Types of servers 110 that may be used by the system 400 include, but are not limited to, search servers, document indexing servers, and web servers, or any combination thereof.

Search servers may include one or more computing entities 200 designed to implement a search engine, such as a documents/records search engine, general webpage search engine, etc. Search servers may, for instance, include one or more web servers designed to receive search queries and/or inputs from users 405, search one or more databases 115 in response to the search queries and/or inputs, and provide documents or information, relevant to the search queries and/or inputs, to users 405. In some implementations, search servers may include a web search server that may provide webpages to users 405, wherein a provided webpage may include a reference to a web server at which the desired information and/or links are located. The references to the web server at which the desired information is located may be included in a frame and/or text box, or as a link to the desired information/document. Document indexing servers may include one or more devices designed to index documents available through networks 150. Document indexing servers may access other servers 110, such as web servers that host content, to index the content. In some implementations, document indexing servers may index documents/records stored by other servers 110 connected to the network 150. Document indexing servers may, for instance, store and index content, information, and documents relating to user accounts and user-generated content. Web servers may include servers 110 that provide webpages to clients 105. For instance, the webpages may be HTML-based webpages. A web server may host one or more websites. As used herein, a website may refer to a collection of related webpages. Frequently, a website may be associated with a single domain name, although some websites may potentially encompass more than one domain name. The concepts described herein may be applied on a per-website basis. Alternatively, in some implementations, the concepts described herein may be applied on a per-webpage basis.

As used herein, a database 115 refers to a set of related data and the way it is organized. Access to this data is usually provided by a database management system (DBMS) consisting of an integrated set of computer software that allows users 405 to interact with one or more databases 115 and provides access to all of the data contained in the database 115. The DBMS provides various functions that allow entry, storage and retrieval of large quantities of information and provides ways to manage how that information is organized. Because of the close relationship between the database 115 and the DBMS, as used herein, the term database 115 refers to both a database 115 and DBMS.

Figure 2:
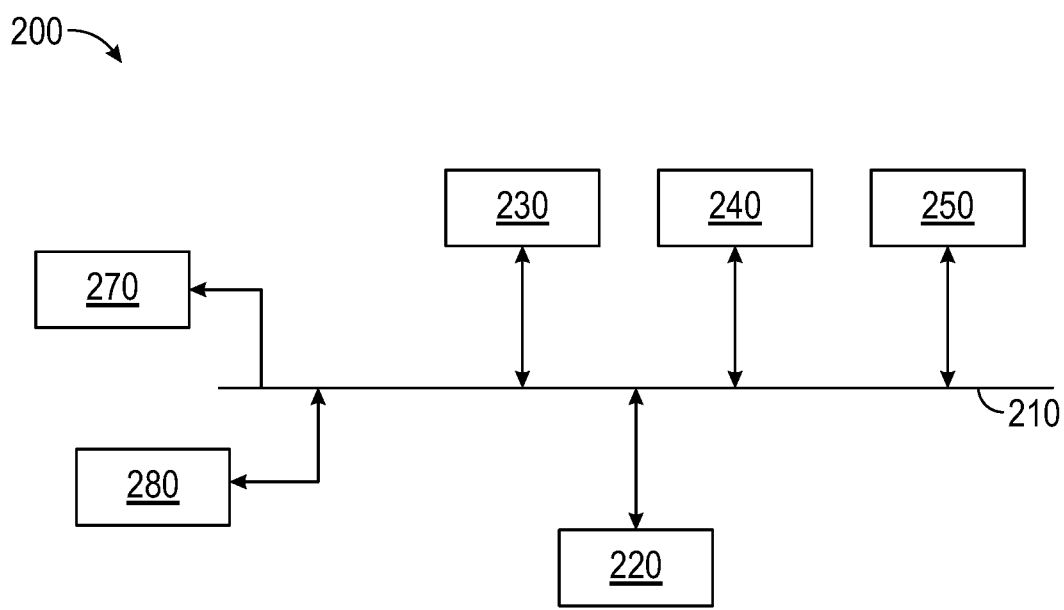
FIG. 2 illustrates a system embodying features consistent with the principles of the present disclosure.

FIG. 2 is an exemplary diagram of a client 105, server 110, and/or or database 115 (hereinafter collectively referred to as "computing entity 200"), which may correspond to one or more of the clients 105, servers 110, and databases 115 according to an implementation consistent with the principles of the invention as described herein. The computing entity 200 may comprise a bus 210, a processor 220, memory 304, a storage device 250, a peripheral device 270, and a communication interface 280 (such as wired or wireless communication device). The bus 210 may be defined as one or more conductors that permit communication among the components of the computing entity 200. The processor 220 may be defined as logic circuitry that responds to and processes the basic instructions that drive the computing entity 200. Memory 304 may be defined as the integrated circuitry that stores information for immediate use in a computing entity 200. A peripheral device 270 may be defined as any hardware used by a user 405 and/or the computing entity 200 to facilitate communicate between the two. A storage device 250 may be defined as a device used to provide mass storage to a computing entity 200. A communication interface 280 may be defined as any transceiver-like device that enables the computing entity 200 to communicate with other devices and/or computing entities 200.

The bus 210 may comprise a high-speed interface 308 and/or a low-speed interface 312 that connects the various components together in a way such they may communicate with one another. A high-speed interface 308 manages bandwidth-intensive operations for computing device 300, while a low-speed interface 312 manages lower bandwidth-intensive operations. In some preferred embodiments, the high-speed interface 308 of a bus 210 may be coupled to the memory 304, display 316, and to high-speed expansion ports 310, which may accept various expansion cards such as a graphics processing unit (GPU). In other preferred embodiments, the low-speed interface 312 of a bus 210 may be coupled to a storage device 250 and low-speed expansion ports 314. The low-speed expansion ports 314 may include various communication ports, such as USB, Bluetooth, Ethernet, wireless Ethernet, etc. Additionally, the low-speed expansion ports 314 may be coupled to one or more peripheral devices 270, such as a keyboard, pointing device, scanner, and/or a networking device, wherein the low-speed expansion ports 314 facilitate the transfer of input data from the peripheral devices 270 to the processor 220 via the low-speed interface 312.

The processor 220 may comprise any type of conventional processor or microprocessor that interprets and executes computer readable instructions. The processor 220 is configured to perform the operations disclosed herein based on instructions stored within the system 400. The processor 220 may process instructions for execution within the computing entity 200, including instructions stored in memory 304 or on a storage device 250, to display graphical information for a graphical user interface (GUI) on an external peripheral device 270, such as a display 316. The processor 220 may provide for coordination of the other components of a computing entity 200, such as control of user interfaces 411A, 411B, 511, 711, applications run by a computing entity 200, and wireless communication by a communication interface 280 of the computing entity 200. The processor 220 may be any processor or microprocessor suitable for executing instructions. In some embodiments, the processor 220 may have a memory device therein or coupled thereto suitable for storing the data, content, or other information or material disclosed herein. In some instances, the processor 220 may be a component of a larger computing entity 200. A computing entity 200 that may house the processor 220 therein may include, but are not limited to, laptops, desktops, workstations, personal digital assistants, servers 110, mainframes, cellular telephones, tablet computers, smart televisions, streaming devices, or any other similar device. Accordingly, the inventive subject matter disclosed herein, in full or in part, may be implemented or utilized in devices including, but are not limited to, laptops, desktops, workstations, personal digital assistants, servers 110, mainframes, cellular telephones, tablet computers, smart televisions, smartwatches, streaming devices, or any other similar device.

Memory 304 stores information within the computing device 300. In some preferred embodiments, memory 304 may include one or more volatile memory units. In another preferred embodiment, memory 304 may include one or more non-volatile memory units. Memory 304 may also include another form of computer-readable medium, such as a magnetic, solid state, or optical disk. For instance, a portion of a magnetic hard drive may be partitioned as a dynamic scratch space to allow for temporary storage of information that may be used by the processor 220 when faster types of memory, such as random-access memory (RAM), are in high demand. A computer-readable medium may refer to a non-transitory computer-readable memory device. A memory device may refer to storage space within a single storage device 250 or spread across multiple storage devices 250. The memory 304 may comprise main memory 230 and/or read only memory (ROM) 240. In a preferred embodiment, the main memory 230 may comprise RAM or another type of dynamic storage device 250 that stores information and instructions for execution by the processor 220. ROM 240 may comprise a conventional ROM device or another type of static storage device 250 that stores static information and instructions for use by processor 220. The storage device 250 may comprise a magnetic and/or optical recording medium and its corresponding drive.

As mentioned earlier, a peripheral device 270 is a device that facilitates communication between a user 405 and the processor 220. The peripheral device 270 may include, but is not limited to, an input device and/or an output device. As used herein, an input device may be defined as a device that allows a user 405 to input data and instructions that is then converted into a pattern of electrical signals in binary code that are comprehensible to a computing entity 200. An input device of the peripheral device 270 may include one or more conventional devices that permit a user 405 to input information into the computing entity 200, such as a controller, scanner, phone, camera, scanning device, keyboard, a mouse, a pen, voice recognition and/or biometric mechanisms, etc. As used herein, an output device may be defined as a device that translates the electronic signals received from a computing entity 200 into a form intelligible to the user 405. An output device of the peripheral device 270 may include one or more conventional devices that output information to a user 405, including a display 316, a printer, a speaker, an alarm, a projector, etc. Additionally, storage devices 250, such as CD-ROM drives, and other computing entities 200 may act as a peripheral device 270 that may act independently from the operably connected computing entity 200. For instance, a streaming device may transfer data to a smartphone or smartwatch, wherein the smartphone or smartwatch may use that data in a manner separate from the streaming device.

The storage device 250 is capable of providing the computing entity 200 mass storage. In some embodiments, the storage device 250 may comprise a computer-readable medium such as the memory 304, storage device 250, or memory 304 on the processor 220. A computer-readable medium may be defined as one or more physical or logical memory devices and/or carrier waves. Devices that may act as a computer readable medium include, but are not limited to, a hard disk device, optical disk device, tape device, flash memory or other similar solid-state memory device, or an array of devices, including devices in a storage area network or other configurations. Examples of computer-readable mediums include, but are not limited to, magnetic media such as hard disks, floppy disks, and magnetic tape; optical media such as CD ROM discs and DVDs; magneto-optical media such as optical discs; and hardware devices that are specially configured to store and perform programming instructions, such as ROM 240, RAM, flash memory, and the like.

In an embodiment, a computer program may be tangibly embodied in the storage device 250. The computer program may contain instructions that, when executed by the processor 220, performs one or more steps that comprise a method, such as those methods described herein. The instructions within a computer program may be carried to the processor 220 via the bus 210. Alternatively, the computer program may be carried to a computer-readable medium, wherein the information may then be accessed from the computer-readable medium by the processor 220 via the bus 210 as needed. In a preferred embodiment, the software instructions may be read into memory 304 from another computer-readable medium, such as data storage device 250, or from another device via the communication interface 280. Alternatively, hardwired circuitry may be used in place of or in combination with software instructions to implement processes consistent with the principles as described herein. Thus, implementations consistent with the invention as described herein are not limited to any specific combination of hardware circuitry and software.

Figure 3:
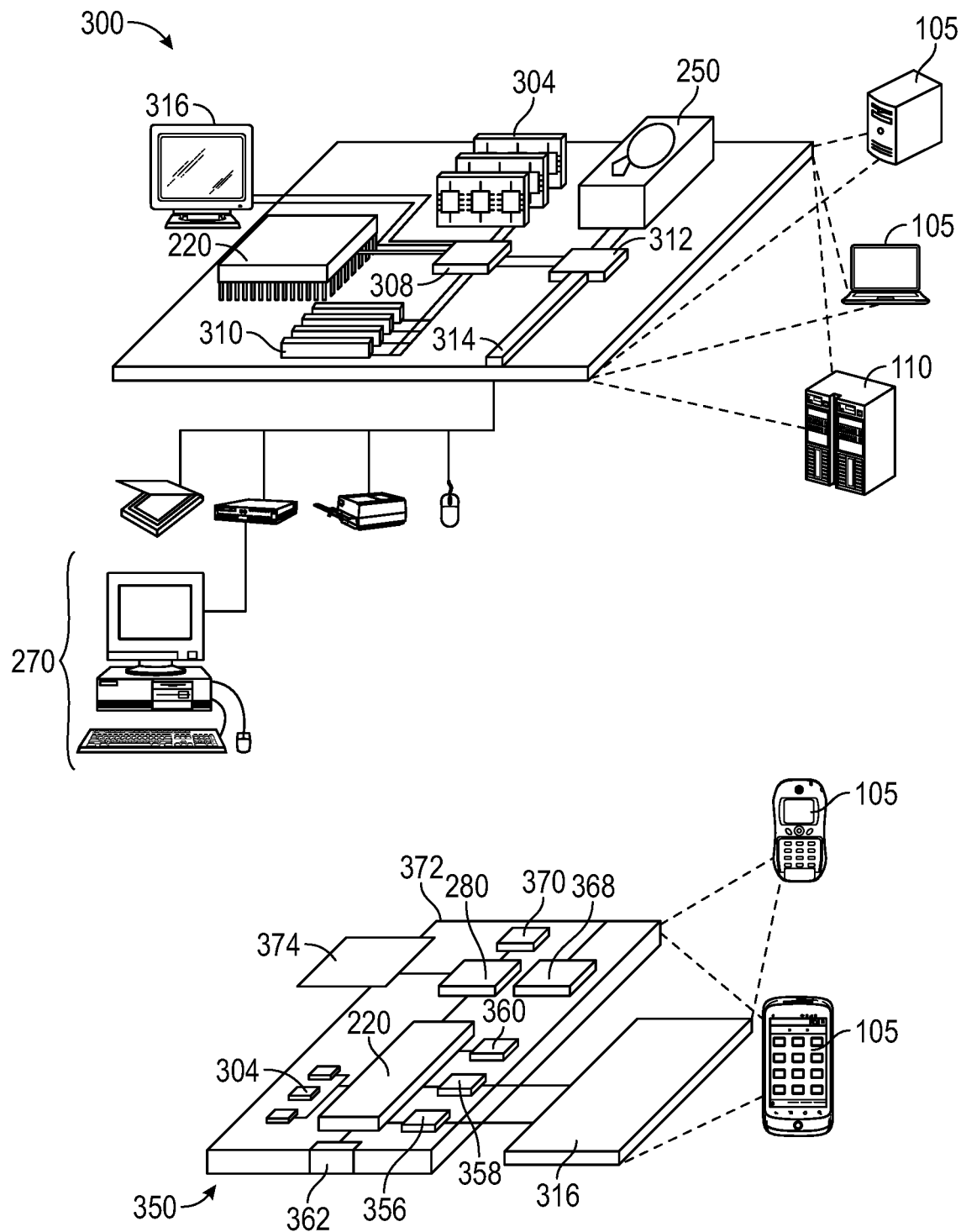
FIG. 3 illustrates a system embodying features consistent with the principles of the present disclosure.

FIG. 3 depicts exemplary computing entities 200 in the form of a computing device 300 and mobile computing device 350, which may be used to carry out the various embodiments of the invention as described herein. A computing device 300 is intended to represent various forms of digital computers, such as laptops, desktops, workstations, servers 110, databases 115, mainframes, and other appropriate computers. A mobile computing device 350 is intended to represent various forms of mobile devices, such as scanners, scanning devices, personal digital assistants, cellular telephones, smart phones, smartwatch, tablet computers, and other similar devices. The various components depicted in FIG. 3, as well as their connections, relationships, and functions are meant to be examples only, and are not meant to limit the implementations of the invention as described herein. The computing device 300 may be implemented in a number of different forms, as shown in FIGS. 1 and 3. For instance, a computing device 300 may be implemented as a server 110 or in a group of servers 110. Computing devices 300 may also be implemented as part of a rack server system. In addition, a computing device 300 may be implemented as a personal computer, such as a desktop computer or laptop computer. Alternatively, components from a computing device 300 may be combined with other components in a mobile device, thus creating a mobile computing device 350. Each mobile computing device 350 may contain one or more computing devices 300 and mobile devices, and an entire system may be made up of multiple computing devices 300 and mobile devices communicating with each other as depicted by the mobile computing device 350 in FIG. 3. The computing entities 200 consistent with the principles of the invention as disclosed herein may perform certain receiving, communicating, generating, output providing, correlating, and storing operations as needed to perform the various methods as described in greater detail below.

In the embodiment depicted in FIG. 3, a computing device 300 may include a processor 220, memory 304 a storage device 250, high-speed expansion ports 310, low-speed expansion ports 314, and bus 210 operably connecting the processor 220, memory 304, storage device 250, high-speed expansion ports 310, and low-speed expansion ports 314. In one preferred embodiment, the bus 210 may comprise a high-speed interface 308 connecting the processor 220 to the memory 304 and high-speed expansion ports 310 as well as a low-speed interface 312 connecting to the low-speed expansion ports 314 and the storage device 250. Because each of the components are interconnected using the bus 210, they may be mounted on a common motherboard as depicted in FIG. 3 or in other manners as appropriate. The processor 220 may process instructions for execution within the computing device 300, including instructions stored in memory 304 or on the storage device 250. Processing these instructions may cause the computing device 300 to display graphical information for a GUI on an output device, such as a display 316 coupled to the high-speed interface 308. In other implementations, multiple processors and/or multiple buses may be used, as appropriate, along with multiple memory units and/or multiple types of memory. Additionally, multiple computing devices may be connected, wherein each device provides portions of the necessary operations.

A mobile computing device 350 may include a processor 220, memory 304 a peripheral device 270 (such as a display 316, a communication interface 280, and a transceiver 368, among other components). A mobile computing device 350 may also be provided with a storage device 250, such as a micro-drive or other previously mentioned storage device 250, to provide additional storage. Preferably, each of the components of the mobile computing device 350 are interconnected using a bus 210, which may allow several of the components of the mobile computing device 350 to be mounted on a common motherboard as depicted in FIG. 3 or in other manners as appropriate. In some implementations, a computer program may be tangibly embodied in an information carrier. The computer program may contain instructions that, when executed by the processor 220, perform one or more methods, such as those described herein. The information carrier is preferably a computer-readable medium, such as memory, expansion memory 374, or memory 304 on the processor 220 such as ROM 240, that may be received via the transceiver or external interface 362. The mobile computing device 350 may be implemented in a number of different forms, as shown in FIG. 3. For instance, a mobile computing device 350 may be implemented as a cellular telephone, part of a smart phone, smartwatch, personal digital assistant, or other similar mobile device.

The processor 220 may execute instructions within the mobile computing device 350, including instructions stored in the memory 304 and/or storage device 250. The processor 220 may be implemented as a chipset of chips that may include separate and multiple analog and/or digital processors. The processor 220 may provide for coordination of the other components of the mobile computing device 350, such as control of the user interfaces 411A, 411B, 511, 711, applications run by the mobile computing device 350, and wireless communication by the mobile computing device 350. The processor 220 of the mobile computing device 350 may communicate with a user 405 through the control interface 358 coupled to a peripheral device 270 and the display interface 356 coupled to a display 316. The display 316 of the mobile computing device 350 may include, but is not limited to, Liquid Crystal Display (LCD), Light Emitting Diode (LED) display, Organic Light Emitting Diode (OLED) display, and Plasma Display Panel (PDP), holographic displays, augmented reality displays, virtual reality displays, or any combination thereof. The display interface 356 may include appropriate circuitry for causing the display 316 to present graphical and other information to a user 405. The control interface 358 may receive commands from a user 405 via a peripheral device 270 and convert the commands into a computer readable signal for the processor 220. In addition, an external interface 362 may be provided in communication with processor 220, which may enable near area communication of the mobile computing device 350 with other devices. The external interface 362 may provide for wired communications in some implementations or wireless communication in other implementations. In a preferred embodiment, multiple interfaces may be used in a single mobile computing device 350 as is depicted in FIG. 3.

Memory 304 stores information within the mobile computing device 350. Devices that may act as memory 304 for the mobile computing device 350 include, but are not limited to computer-readable media, volatile memory, and non-volatile memory. Expansion memory 374 may also be provided and connected to the mobile computing device 350 through an expansion interface 372, which may include a Single In-Line Memory Module (SIM) card interface or micro secure digital (Micro-SD) card interface. Expansion memory 374 may include, but is not limited to, various types of flash memory and non-volatile random-access memory (NVRAM). Such expansion memory 374 may provide extra storage space for the mobile computing device 350. In addition, expansion memory 374 may store computer programs or other information that may be used by the mobile computing device 350. For instance, expansion memory 374 may have instructions stored thereon that, when carried out by the processor 220, cause the mobile computing device 350 perform the methods described herein. Further, expansion memory 374 may have secure information stored thereon; therefore, expansion memory 374 may be provided as a security module for a mobile computing device 350, wherein the security module may be programmed with instructions that permit secure use of a mobile computing device 350. In addition, expansion memory 374 having secure applications and secure information stored thereon may allow a user 405 to place identifying information on the expansion memory 374 via the mobile computing device 350 in a non-hackable manner.

A mobile computing device 350 may communicate wirelessly through the communication interface 280, which may include digital signal processing circuitry where necessary. The communication interface 280 may provide for communications under various modes or protocols, including, but not limited to, Global System Mobile Communication (GSM), Short Message Services (SMS), Enterprise Messaging System (EMS), Multimedia Messaging Service (MMS), Code Division Multiple Access (CDMA), Time Division Multiple Access (TDMA), Personal Digital Cellular (PDC), Wideband Code Division Multiple Access (WCDMA), IMT Multi-Carrier (CDMAX 0), and General Packet Radio Service (GPRS), or any combination thereof. Such communication may occur, for example, through a transceiver 368. Short-range communication may occur, such as using a Bluetooth, WIFI, or other such transceiver 368. In addition, a Global Positioning System (GPS) receiver module 370 may provide additional navigation- and location-related wireless data to the mobile computing device 350, which may be used as appropriate by applications running on the mobile computing device 350. Alternatively, the mobile computing device 350 may communicate audibly using an audio codec 360, which may receive spoken information from a user 405 and covert the received spoken information into a digital form that may be processed by the processor 220. The audio codec 360 may likewise generate audible sound for a user 405, such as through a speaker, e.g., in a handset of mobile computing device 350. Such sound may include sound from voice telephone calls, recorded sound such as voice messages, music files, etc. Sound may also include sound generated by applications operating on the mobile computing device 350.

The system 400 may also comprise a power supply. The power supply may be any source of power that provides the system 400 with power. In an embodiment, the power supply may be a stationary power outlet. The system 400 may comprise of multiple power supplies that may provide power to the system 400 in different circumstances. For instance, the system 400 may be directly plugged into a stationary power outlet, which may provide power to the system 400 so long as it remains in one place. However, the system 400 may also be connected to a backup battery so that the system 400 may receive power even when the power supply is not connected to a stationary power outlet or if the stationary power outlet ceases to provide power to the system 400.

Figure 4:
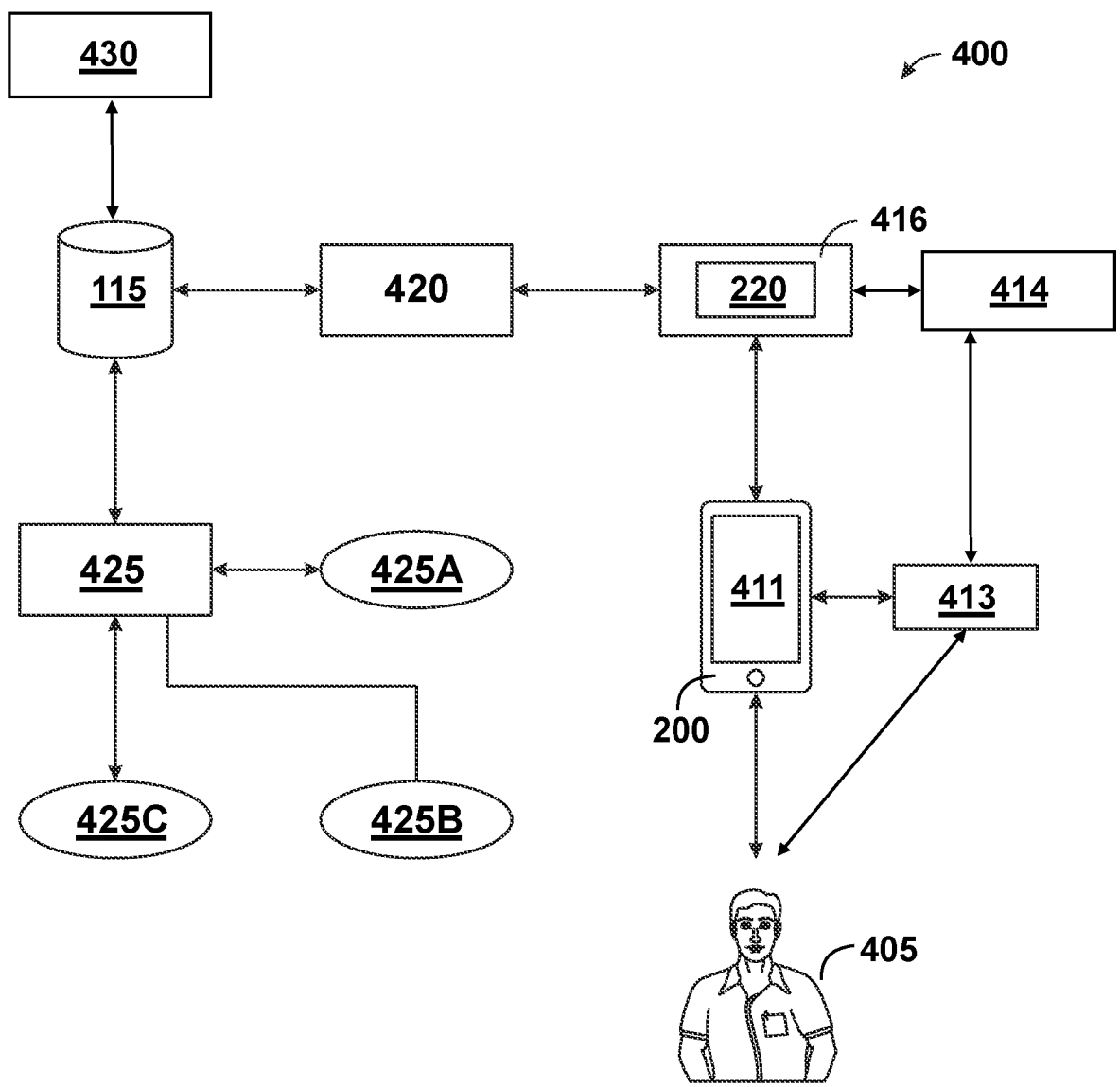
FIG. 4 illustrates a system embodying features consistent with the principles of the present disclosure.
Figure 5:
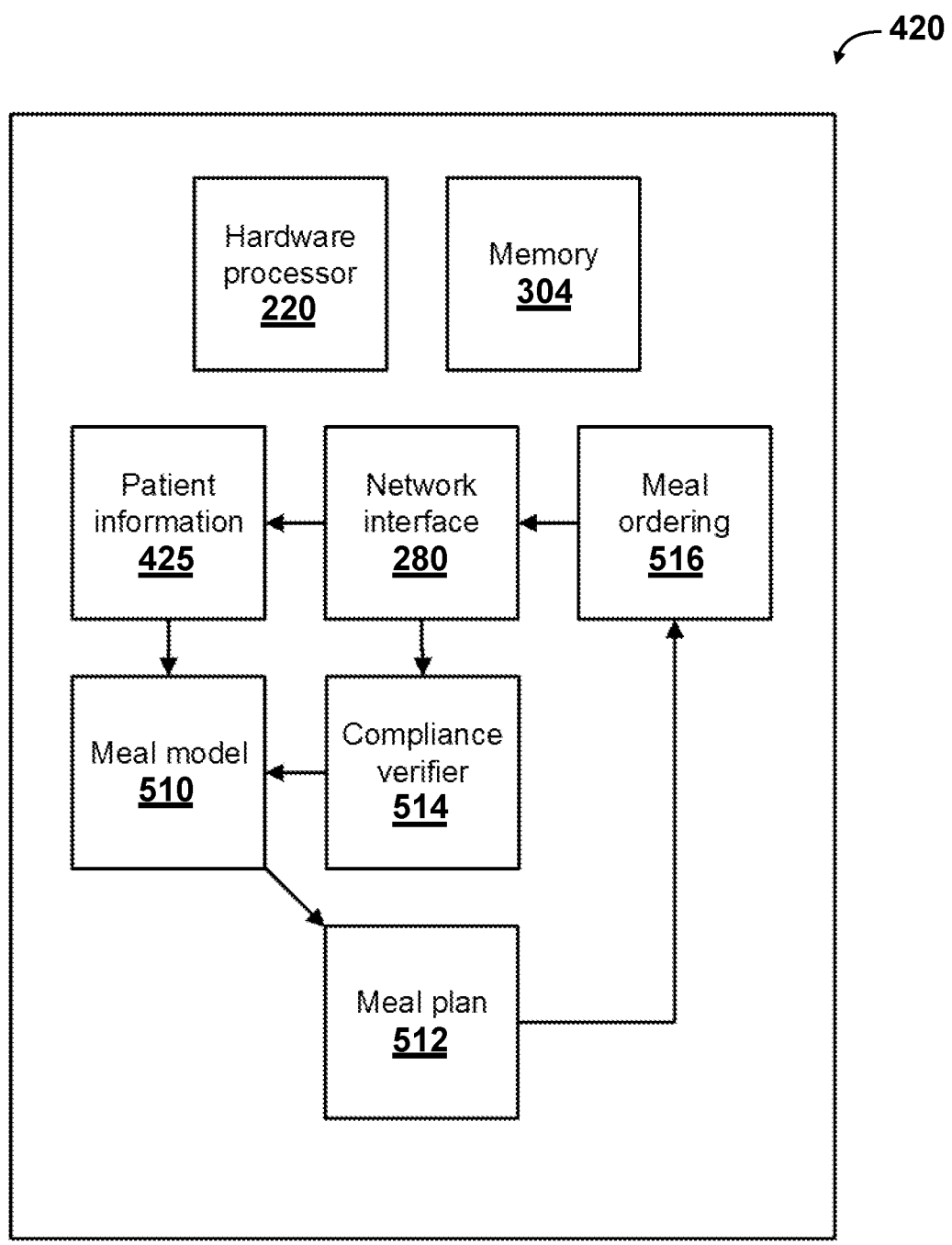
FIG. 5 illustrates a system embodying features consistent with the principles of the present disclosure.
Figure 6:
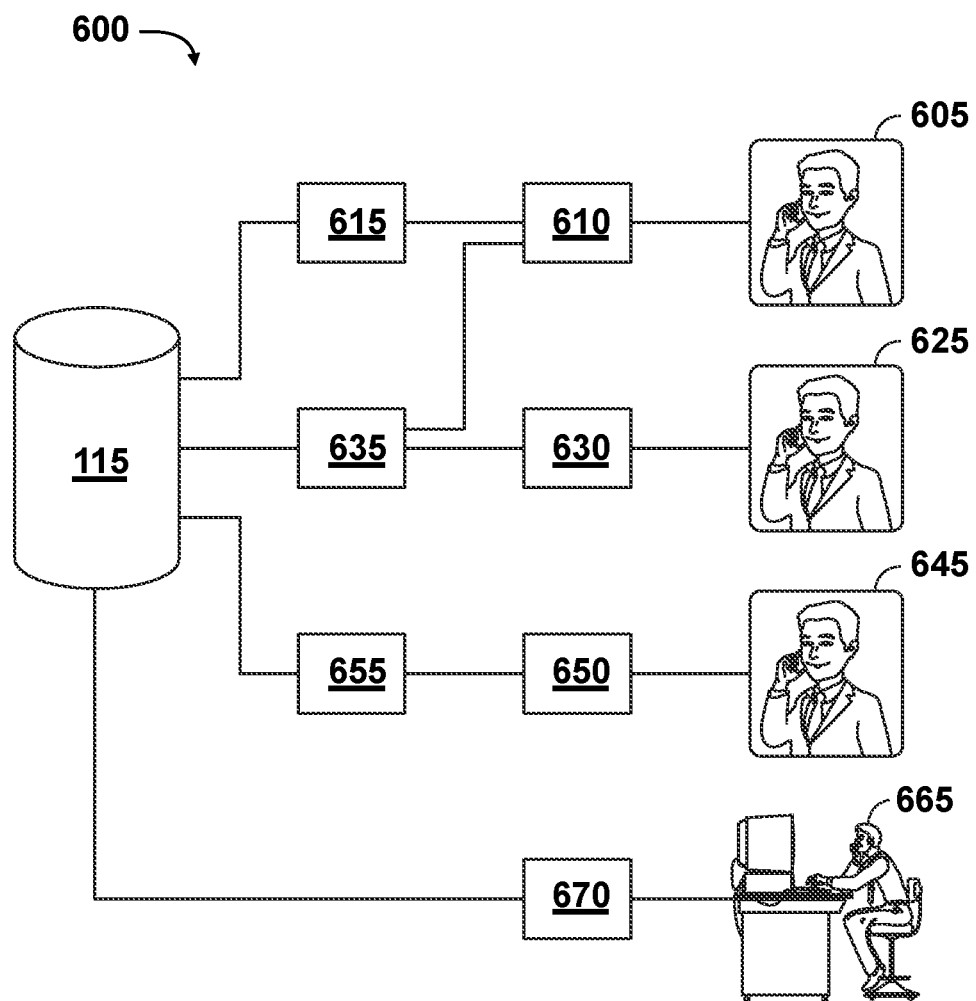
FIG. 6 is a diagram illustrating the manner in which individual access to data may be granted or limited based on user roles and administrator roles.
Figure 7:
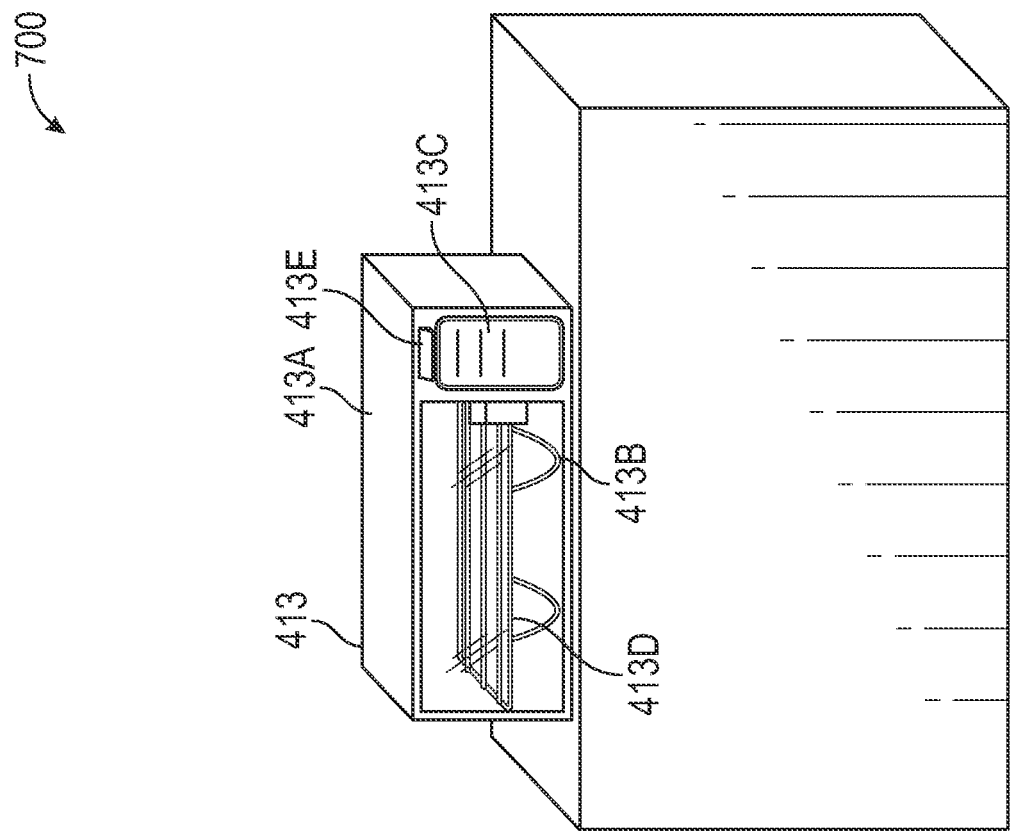
FIG. 7 illustrates an example environment in which a user may use the system and implement the techniques of the present disclosure.
Figure 7:
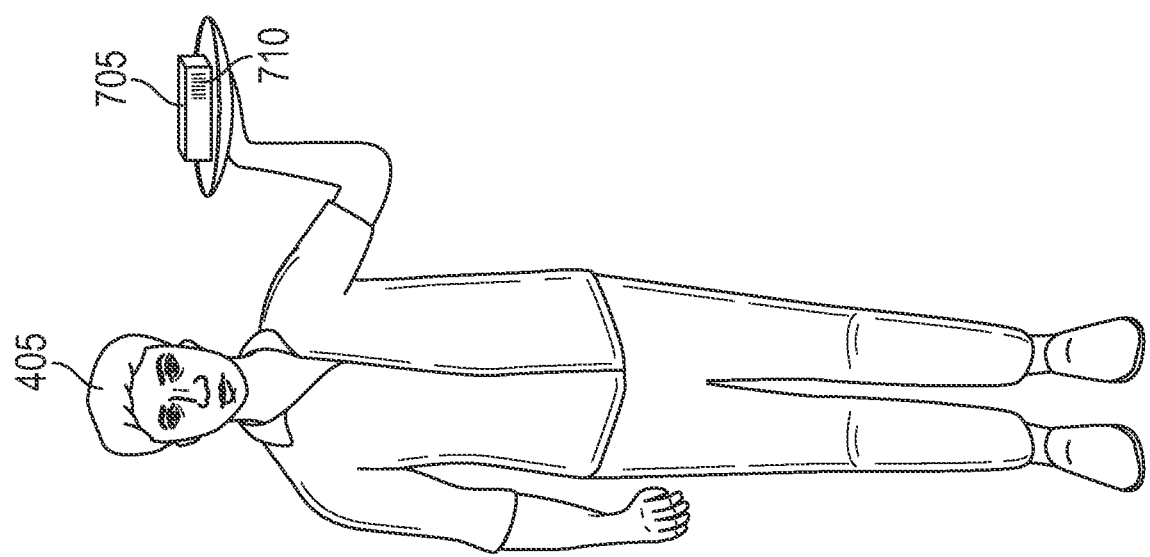
Figure 8:
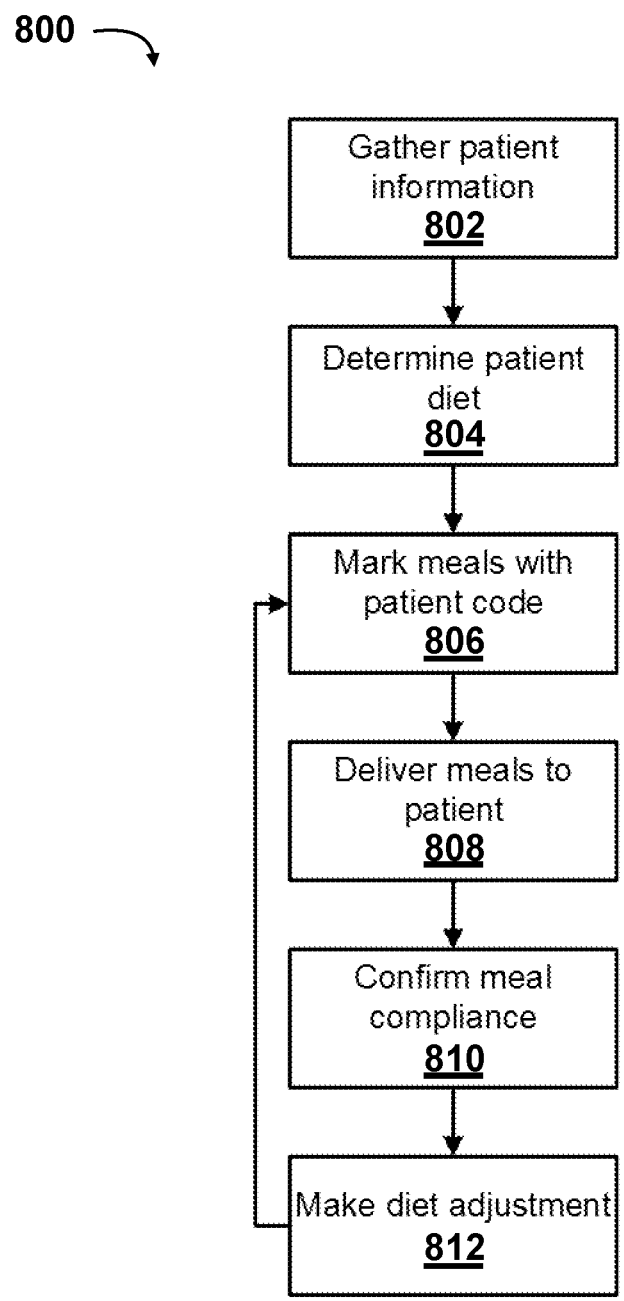
FIG. 8 is a flow chart illustrating certain method steps of a method embodying features consistent with the principles of the present disclosure.

FIGS. 4-8 illustrate a system 400 and method for tracking and delivering prepared meals 705 to individuals, based on their specific dietary and healthcare needs. In addition, implementations of the present principles provide for tracking of diet compliance by the user 405 in order to assist a caregiver to tailor subsequent food deliveries and provide foods that the user 405 finds more palatable. FIG. 4 illustrates a preferred embodiment of the system 400 that can be used by a healthcare professional to determine that a user 405 is getting proper nutrition from prepared meals 705. FIG. 5 illustrates the preferred embodiment of a server configured to manage data generated by the system 400. FIG. 6 illustrates permission levels that may be utilized by the present system 400 for controlling access to user content 615, 635, 655 such as user data 425A, patient data 425B, and meal plan data 425C. FIG. 7 illustrates the system 400 being used by a user 405 within an environment 700. FIG. 8 illustrates a method that may be carried out by the system 400. It is understood that the various method steps associated with the methods of the present disclosure may be carried out as operations by the system 400 illustrated in FIGS. 4-7.

As illustrated in FIG. 4, the system 400 generally comprises a computing entity 200 having a user interface 411, diet server 420, meal delivery service 414, smart oven 413, processor 220 operably connected to the computing entity 200 and smart oven 413, and a non-transitory computer-readable medium 416 coupled to the processor 220 and having instructions stored thereon that cause the system 400 to perform the operations described herein. In one preferred embodiment, a user 405 communicates with a diet server 420 using their computing entity 200, inputting health information, meal preference information, and any other information that may be appropriate to determining an appropriate meal plan. The diet server 420 then generates meal data and a meal plan using the meal data 430, and, in accordance with the user's 405 medical conditions, nutritional needs, and preferences, sends an order to meal delivery service 414 for at least one prepared meal 705 contained within said meal plan.

The smart oven 413 generally comprises a heating body 413A, control board, switch, power supply, heating elements 413B, at least one sensor, and charging ports. Other preferred embodiments may further comprise a touch screen display 413C configured to present a user interface 411 to a user 405. Generally, a prepared meal 705 is inserted into the internal cavity of the heating body 413A so that it may be heated by heating elements 413B based on cooking instructions. Heating elements 413B within the heating body 413A increase the temperature until at least one sensor determines that the desired temperature has been reached within the cavity. The control board then regulates the flow of power to the heating elements 413B from the power supply to maintain the desired temperature until a desired period of time has elapsed. Once the cooking cycle is complete, a switch of the control board may break the circuit, thus ceasing the flow of power to the heating elements 413B and preventing them from continuing heating the internal cavity. In a preferred embodiment, the desired temperature, method (bake, broil, etc), and length of time a prepared meal 705 is heated in the smart oven 413 depends on the cooking instructions for the prepared meal 705. For instance, the smart oven 413 may receive cooking instructions that instruct it to heat a lasagna for a longer period of time and at a higher temperature whereas a chicken dish may require a shorter period of time at a lower temperature.

The heating body 413A comprises racks 413D on which a prepared meal 705 sits and houses the various components of the smart oven 413. In a preferred embodiment, the heating body 413A is a metal box having an insulative material within its walls that help the smart oven 413 maintain a consistent temperature while cooking a prepared meal 705. The control board comprises at least one circuit and microchip. The control board may regulate the transfer of power to the various elements of the device, control the temperature of the internal cavity, detect the presence of a prepared meal 705, process a scanned patient and/or meal code received from a scanning device 413E, and control cooking cycles by regulating the power transferred to the heating elements 413B. The control board may send data to a diet server 420 and or database 115 so that it may be stored in user profiles 425 of the system 400. In some preferred embodiments, the control board may execute the various modules described herein so that it may perform the functions of the system 400 without the need of an additional computing entity 200 or diet server 420.

The microchip of the control board comprises a microprocessor, antenna, and memory. The microprocessor may be defined as a multipurpose, clock driven, register based, digital-integrated circuit which accepts binary data as input, processes it according to instructions stored in its memory, and provides results as output. In a preferred embodiment, the microprocessor may receive a signal to start the cooking process from a switch operably connected to the control board, wherein the switch completes a circuit of the control board when the door of the heating body 413A is closed by a user 405. Alternatively, the microprocessor may receive instructions from a computing device via an antenna to start a cooking cycle, wherein the cooking instructions for said cooking cycle are saved within the memory 304 and executed by the microprocessor after the scanning of a patient and/or meal code. For instance, a scanning device 413E may transmit a meal code to the microprocessor of the microchip via the antenna, which causes the microprocessor to retrieve cooking instructions from the memory that instruct the processor in how to carry out said cooking cycle.

A meal delivery service 414 prepares the ordered prepared meal 705 and may also apply one or more meal codes to the prepared meal 705. The meal delivery service 414 may then deliver the prepared meal 705 directly to the user's 405 home and/or make the prepared meal 705 available for patient pickup. A meal delivery service 414 may be any appropriate meal delivery service 414 or system 400. In some cases, it is envisioned that a meal delivery service 414 may be operated by an entity that is distinct from the operator of the diet server 420. For instance, an assisted living facility may have their own meal delivery service 414 that uses the system 400 to design meal plans for its residents that are made in house. However, it is also contemplated that the meal delivery service 414 may be performed by the same entity. For instance, both the diet server 420 and meal delivery service 414 may be operated by a hospital. In yet another embodiment, the meal delivery service 414 may be an entity that contracts with the operator of the diet server 420 to fulfill meal plans by producing prepared meals 705 that may be purchased at a $3^{rd}$ party retailer. For instance, a meal delivery service 414 may make prepared meals 705 created by the system and sell them at a local supermarket.

When the user 405 receives the prepared meal 705, the user 405 uses their computing entity 200 to confirm compliance with the diet. In some embodiments, the patient's computing entity 200 may have a scanning device 413E that allows them to scan a meal code on the prepared meal 705, take a picture of the prepared meal 705, or otherwise acquire evidence that the user 405 has received and consumed the prepared meal 705. In some embodiments, the patient's computing entity 200 can operably connect to a smart oven 413 to register that the prepared meal 705 was duly prepared. In some embodiments, a smart oven 413 can operate independent of the patient's computing entity 200. Although it is specifically contemplated that the patient's computing entity 200 may be a smartphone, it should be understood that any appropriate device may fill this role, such as a laptop or desktop computer or a smart watch.

In some embodiments, a smart oven 413 may have the ability to scan the code(s) applied to a prepared meal 705, and to transmit that information directly to the diet server 420. The smart oven 413 can automatically configure itself to prepare the prepared meal 705, for example setting an appropriate temperature and duration, based on information about the prepared meal 705 that is stored in the smart oven 413, or that is acquired from the diet server 420. Thus, the patient's computing entity 200 and/or smart oven 413 communicate compliance information, along with any recorded patient preference information, back to diet server 420, which may use this information to revise the meal plan for a future prepared meal 705.

In a preferred embodiment, the various data of the system 400 may be stored in user profiles 425. Types of data that may be stored within user profiles 425 of the system 400 include, but are not limited to, user data 425A, patient data 425B, and meal plan data 425C. One preferred embodiment of the system 400 may comprise a database 115 operably connected to the processor 220. The database 115 may be configured to store user data 425A, patient data 425B, and meal plan data 425C within said user profiles 425. As used herein, user data 425A may be defined as personal information of a user 405 that helps the system 400 identify the user 405. Types of data that may be used by the system 400 as user data 425A includes, but is not limited to, a user's name, username, social security number, phone number, gender, age, food preferences, or any combination thereof. As used herein, patient data 425B is data related to a patient's medical history, which may usually be found within an electronic health record. Types of data that may be used by the system 400 as patient data 425B includes, but is not limited to, encounter notes, lab/image reports, medications, diagnoses, assessments, pathological reports, or any combination thereof. As used herein, meal plan data 425C is data related to a meal plan generated by the system 400 for a user 405 based on user data 425A, patient data 425B, compliance verifier module 514, etc. The database 115 may also be configured to store meal data 430 of the system 400, which generated by the meal model module 510 when creating prepared meal 705 for one or more users 405. Meal data 430 may be defined as the contents and nutritional information for a particular prepared meal 705 that meal delivery service 414 may provide a user 405. In some preferred embodiments, meal data 430 may also include preparation instructions that the meal delivery service 414 may use to produce the prepared meals prepared meal 705.

FIG. 5 illustrates the diet server 420 to be used by the system 400. The diet server 420 includes a hardware processor 220 and memory 304. A communication interface 280 facilitates communication between the user 405, user's computing entity 200, meal delivery service 414, and smart oven 413 via any appropriate wired or wireless communications medium and protocol. One or more functional modules may be implemented in the form of, e.g., software that is stored in the memory and that is executed by the hardware processor 220. One or more of the functional modules may alternatively be implemented in the form of one or more discrete hardware components, for example in the form of ASICs or FPGAs.

Patient data 425A within a user profile 425 is received by the communication interface 280 (or input directly through a user interface 411) and may be stored in the memory 304. A meal model 510 may use the data within a user profile 425 to develop a personalized meal plan for a user 405, which may be stored within a user's user profile 425 as meal plan data 425A. The meal model module 510 may be implemented as, for example, a set of heuristics and/or a trained machine learning model, such as a neural network system 400. In some embodiments, the meal model module 510 may embody certain fixed dietary principles, while including a trainable component that takes into account a patient's particular preferences.

The meal plan module 510 outputs a meal plan using prepared meals 705 created by a meal delivery service 414 as directed by the meal model module 510. The meal ordering module 516 then uses the meal plan to order at least one prepared meal 705 for the user 405, for example by communicating with a meal delivery service 414 via the communication interface 280. In addition to sending instructions regarding the at least one prepared meal 705 to be delivered by the meal delivery service 414, the meal ordering module 516 may also send information relating to the patient and/or meal code that is to be applied to the meal. Therefore, the meal ordering module 516 coordinates the construction of prepared meals 705 by the meal delivery service 414 in a way that allows a user 405 of the system 400 to more easily comply with the meal plan.

In another preferred embodiment, a user 405 may input a palatability score into a user interface 411 of the system 400 to assist the meal plan module 512 in designing meal plans for said user 405. The palatability score is preferably comprised of a grading scheme of the meal model module 512 that allows a user 405 to rate a prepared meal using a plurality of categories. These categories include, but are not limited to taste, smell, texture, presentation, price, freshness, or any combination thereof. In some preferred embodiments, the meal model module 512 may create a degree of palatability for a prepared meal 705 using the palatability scores generated by a plurality of users 405 who have graded the prepared meal 705, which may assist a meal delivery service 414 when evaluating whether to continue to make a certain prepared meal 705.

The compliance verifier module 514 receives information from the user 405, patient's computing entity 200, and/or the smart oven 413 that relates to the patient's compliance with the meal plan. In a preferred embodiment, the compliance verifier module 514 creates a degree of compliance for a particular user 405 of the system 400 and relays this information to the meal model module 510 and/or meal plan module 512 to assist with the future construction of meal plans for the user 405. For instance, the compliance verifier module 514 may determine that a user 405 is not eating a particular prepared meal 705, which is making them less compliant than they otherwise might be. The compliance verifier module 514 may then transmit a computer readable signal to the meal model module 510 and/or meal plan module 512 that may cause the meal plan module 512 to choose a new prepared meal 705 and/or to retrain a trainable part of the meal model module 510 to better accommodate the user 405 in the future.

In another preferred embodiment, the compliance verifier module 514 may compare the degree of compliance with a threshold limit to determine whether there is enough cause for concern to involve a medical professional. For instance, the system 400 may determine that a user 405 has been compliant with a meal plan over a three-month period but has been non-compliant over the last three days. This may cause the compliance verifier module 514 to send a computer readable signal to a medical professional's computing entity 200 and instruct said medical professional to reach out to said patient. A lower limit of the threshold limit may be compared to the degree of compliance before the compliance verifier module 514 determines action is needed. For instance, the compliance verifier module 514 may have a threshold limit with a lower limit of 80% compliance before the compliance verifier module 514 sends a computer readable signal to a medical professional's computing entity 200 requesting intervention.

In one preferred embodiment, a user interface 411 of the medical professional's computing entity 200 may interlink with the user interface 411 of the smart oven 413 and/or user's computing entity 200 to initiate communication with the user 405 when the user 405 is not compliant with their meal plan. This may allow the medical professional to directly assess a patient to determine whether the user 405 is experiencing any health-related issues that might be causing the user 405 to have a lower compliance with the meal plan. The medical professional may then make notes within their user interface 411 that may be saved as patient data 425B by the system 400, which may then be used to adjust the meal plan to help the patient become more compliant. For instance, a medical professional may note that a particular user 405 enjoys the taste and texture of the prepared meals 705 within the user's 405 designed meal plan; however, the prepared meals 705 may be causing digestive issues for the user 405, which could reveal that the user 405 has a new or previously undiagnosed food allergy. In a preferred embodiment, the system 400 may use machine learning techniques to assist the medical professional determine such health issues using the data of the system 400.

In another preferred embodiment, patients may be awarded compliance points when complying with a meal plan, which may be saved within a user's 405 user profile 425 as patient data 425B. These compliance points may then be used to purchase prepared meals 705 so that the user 405 is encouraged to continue to comply with the meal plan. For instance, in one preferred embodiment, a user 405 having 50 compliance points in their user profile 425 may be rewarded 100 more compliance points for eating a prepared meal 705 that is part of their meal plan, bringing their total amount of compliance points within their user profile 425 to 150. A prepared meal 705 costing 150 compliance points may then be purchased by the user 405. Alternatively, the user 405 may save those compliance points so that they may purchase a prepared meal 705 costing 250 compliance points at a later date. In other preferred embodiments, compliances points awarded for compliance with one's meal plan may be joined with other "good health" point systems. For instance, compliance points may be combined with points rewarded for exercise, mindfulness, standing at hourly intervals, etc.

As mentioned previously, the system 400 may further comprise a user interface 411. A user interface 411 may be defined as a space where interactions between a user 405 and the system 400 may take place. In an embodiment, the interactions may take place in a way such that a user 405 may control the operations of the system 400. A user interface 411 may include, but is not limited to operating systems, command line user interfaces, conversational interfaces, web-based user interfaces, zooming user interfaces, touch screens, task-based user interfaces, touch user interfaces, text-based user interfaces, intelligent user interfaces, brain-computer interfaces (BCIs), and graphical user interfaces, or any combination thereof. The system 400 may present data of the user interface 411 to the user 405 via a display 316 operably connected to the processor 220. A display 316 may be defined as an output device that communicates data that may include, but is not limited to, visual, auditory, cutaneous, kinesthetic, olfactory, and gustatory, or any combination thereof.

The smart oven 413 preferably comprises a control board, heat insulated container, heating elements 413B, and a control panel. In a preferred embodiment, the control panel is a touch screen display 413C that may also be used by the system 400 to facilitate communication between a user 405 and a medical professional. The smart oven 413 may be operably connected to the user's computing entity 200 in a way that allows a user 405 to input cooking instructions for a particular prepared meal 705. In one preferred embodiment, the user 405 may scan a meal code of a prepared meal 705 using a scanning device 413E and user interface 411 of their computing entity 200, which may cause the computing entity to send a computer readable signal to the smart oven 413 containing cooking instructions. Alternatively, a control panel of the smart oven 413 may allow a user 405 to select a prepared meal 705 from a plurality of prepared meals 705, wherein selection of the prepared meal 705 causes the processor 220 to retrieve cooking instructions from memory 304. In other preferred embodiments, a scanning device 413E of the smart oven 413, such as a camera or RFID reader, allows a user 405 to scan a code on the prepared meal 705, which may cause the processor 220 to retrieve the cooking instructions.

These cooking instructions may comprise steps for cooking a particular prepared meal 705. For instance, the cooking instructions smart oven 413 may require that a plastic film of the meal be left on while the smart oven 413 bakes the prepared meal 705 at a certain temperature before instruction the user 405 to remove the plastic film so that the smart oven 413 can broil the prepared meal 705 until finished. These instructions may be relayed to the user 405 so that the user 405 may assist the smart oven 413 cook the prepared meal 705 in the manner described, allowing for better quality meals. In one preferred embodiment, the smart oven 413 may alert a user 405 when assistance is needed to complete a particular step. For instance, an output device of the smart oven 413 may emit and audible alarm to alert the user 405 to remove the plastic film. In another preferred embodiment, the user's computing entity 200 operably connected to the smart oven 413 may alert the user 405 to perform a particular step during the cooking process.

To prevent un-authorized user 405 from accessing other user's 405 information, the system 400 may employ a security method. As illustrated in FIG. 6, the security method of the system 400 may comprise a plurality of permission levels 600 that may grant users 405 access to user content 615, 635, 655 within the database 115 while simultaneously denying users 405 without appropriate permission levels 600 the ability to view user content 615, 635, 655. To access the user content 615, 635, 655 stored within the database 115, users 405 may be required to make a request via a user interface 411. Access to the data within the database 115 may be granted or denied by the processor 220 based on verification of a requesting user's 605, 625, 645 permission level 600. If the requesting user's 605, 625, 645 permission level 600 is sufficient, the processor 220 may provide the requesting user 605, 625, 645 access to user content 615, 635, 655 stored within the database 115. Conversely, if the requesting user's 605, 625, 645 permission level 600 is insufficient, the processor 220 may deny the requesting user 605, 625, 645 access to user content 615, 635, 655 stored within the database 115. In an embodiment, permission levels 600 may be based on user roles 610, 630, 650 and administrator roles 670, as illustrated in FIG. 6. User roles 610, 630, 650 allow requesting users 605, 625, 645 to access user content 615, 635, 655 that a user 405 has uploaded and/or otherwise obtained through use of the system 400. Administrator roles 670 allow administrators 665 to access system 400 wide data.

In an embodiment, user roles 610, 630, 650 may be assigned to a user in a way such that a requesting user 605, 625, 645 may view user profiles 425 containing user data 425A, patient data 425B, and meal plan data 425C via a user interface. To access the data within the database 115, a user 405 may make a user request via the user interface 411 to the processor 220. In an embodiment, the processor 220 may grant or deny the request based on the permission level 600 associated with the requesting user 605, 625, 645. Only users 405 having appropriate user roles 610, 630, 650 or administrator roles 670 may access the data within the user profiles 425. For instance, as illustrated in FIG. 6, requesting user 1 605 has permission to view user 1 content 615 and user 2 content 635 whereas requesting user 2 625 only has permission to view user 2 content 635. Alternatively, user content 615, 635, 655 may be restricted in a way such that a user 405 may only view a limited amount of user content 615, 635, 655. For instance, requesting user 3 645 may be granted a permission level 600 that only allows them to view user 3 content 655 related to their specific compliance records but not user 3 content 655 related to other patient data 425B. In the example illustrated in FIG. 6, an administrator 665 may bestow a new permission level 600 on users 405 so that it may grant them greater permissions or lesser permissions. For instance, an administrator 665 may bestow a greater permission level 600 on other users so that they may view user 3's content 655 and/or any other user's 405 content 615, 635, 655. Therefore, the permission levels 600 of the system 400 may be assigned to users 405 in various ways without departing from the inventive subject matter described herein.

FIG. 8 illustrates a flow diagram 800 regarding a method for delivering prepared meals 705 to patients in accordance with their specific dietary needs. Block 802 gathers information about the patient. This information may come from a variety of different sources. The information may include, for example, coded problem lists (using, e.g., current procedural terminology (CPT) codes, international classification of diseases (ICD) codes, etc.), procedure lists, allergies to foods and medications, lists of active medications, lab results, patient medical history, patient social history (e.g., including information relating to languages spoken, cognitive abilities, living conditions, availability of transportation, etc.), physician orders with respect to diet, a dietician's assessment and recommendations, and any other appropriate source. This information can be drawn from, for example, hospital and ambulatory clinic health records, insurer information, and state health information exchanges.

Block 804 determines an appropriately healthy diet for the patient, which will provide for the patient's specific dietary and medical needs. Toward this end, block 804 may identify a meal plan that includes a set of needs that are tailored to the patient's condition, for example providing an appropriate calorie amount, with sufficient vitamins and other nutrients for the patient to thrive. The meal plan determined by block 804 may also establish dietary prohibitions and limitations, for example by imposing a sodium limit for patients with hypertension, or by prohibiting foods that the patient is allergic to or has expressed a dislike for. A caloric range, including a minimum and a maximum, may be set, based on the patient's needs and activity level. Based on these needs and limits, block 804 may select from a plurality of matching prepared meals 705, which comply with the needs, prohibitions, and limitations set out in the meal plan. The prepared meals 705 that make up the set may be predetermined, for example with menus being created by a nutritionist and chef, or they may be selected by a patient or healthcare provider a la carte, as long as all of the requirements of the meal plan are met. Patient preferences may also be stored and used to guide the selection of the prepared meals 705.

While it is specifically contemplated that a meal plan may be formulated for patients having particularly diet-sensitive conditions, such as Crohn's disease, gout, or celiac disease, the present principles can be used for any person who might benefit from diet tracking and/or meal delivery service 414. Even in the absence of a specific medical condition, a healthy diet has a useful prophylactic effect. The present principles may therefore be used by the elderly and those in food-challenged areas to maintain good nutrition. The present principles may also be used for individuals who have diet goals such as, for example, losing weight or building muscle mass. The present principles may also be used for individuals who are confined to their homes for any reason.

Block 806 marks a selected prepared meal 705 with an appropriate patient code and/or meal code. These codes may be uniquely identifying serial numbers, bar codes, QR codes, or any other appropriate codes to associate the prepared meal 705 with the patient. The code may be applied to the prepared meal 705 by any appropriate mechanism, for example by printing a label that may be affixed to meal packaging, or by printing the code directly onto the meal packaging itself. In some cases, the prepared meal 705 may include multiple distinct parts, which may be delivered and prepared as separate packages. In such cases, block 806 may apply a distinct code to each part, making it possible to determine which parts of a prepared meal 705 were consumed, and which were not. In some embodiments, the patient and the particular prepared meal 705 may be identified in separate codes applied to the prepared meal 705. In other embodiments, a single code may identify both the patient and the prepared meal 705.

Block 808 delivers the prepared meal 705 to the patient. In some cases, the prepared meal 705 may be delivered to the patient in their home. In other cases, the meal may be delivered to a room in a healthcare facility, such as in a hospital. Block 808 may also deliver educational material to the patient that relates to the prepared meal 705 and any dietary matters. The delivery of this educational content may include physical delivery, with the prepared meal 705 itself, but may also, or alternatively, be delivered electronically. This delivery of ongoing educational material helps to keep the patient aware of the general parameters of their diet and to emphasize the health benefits associated with following the plan.

Block 810 monitors patient compliance with the meal plan. This may include determining that the patient did consume all or part of the prepared meal 705 and may include information relating to parts of the prepared meal 705 that were not consumed. In some cases, block 810 may receive feedback from the patient, for example entered into a mobile application or web browser form, providing a self-assessment of how much of the food they ate and whether it matched their preferences. In some cases, block 810 may receive confirmation from a patient via a mobile application, for example using biometric authentication or a scan of the patient's unique identification number or code to confirm the identity of the patient and a picture of the prepared meal 705 taken by the patient to confirm the amount of the prepared meal 705 consumed. In some cases, block 810 may receive confirmation from a smart appliance, such as a smart oven 413, that is capable of identifying the patient code to confirm that the prepared meal 705 was prepared by the correct individual. In addition to diet compliance information, block 812 may also receive information relating to patient behavior and overall health, such as biometric data from a fitness tracker or from a blood sugar sensor.

Based on the information received by block 810, block 812 may make a diet adjustment. For example, if a patient expresses a dislike for a particular prepared meal 705, or consistently fails to consume a particular part of a prepared meal 705, block 812 may prevent that food from being included in future prepared meal 705. Block 806 may then be invoked again, with a new selection of prepared meals 705.

Block 812 may generate a compliance score, which rates the patient's compliance with the meal plan, for example based on nutrition information and biometric data. In addition to its use for making adjustments to the meal plan, the compliance score may be used to help incentivize the patient. For example, a high compliance score may be used to by the patient's health insurer to provide or increase reimbursement for some or all of the cost of the patient's prepared meals 705, whereas a lower compliance score may result in a lower or no reimbursement rate. The patient may therefore be informed regarding their compliance score(s).

The compliance score may include, for example, a prescription component, a nutrition component, a fitness component, and any number of additional components. The prescription component may indicate a degree of compliance relating to prescribed medications, the nutrition component may indicate a degree of compliance relating to prescribed dietary measures, and the fitness component may indicate a degree of compliance with a prescribed fitness regimen. These different components may be weighted differently, in accordance with their importance to a particular patient's health.

In some cases, additional intervention may be needed. For example, if block 812 shows that the patient does not consume the prepared meal 705 on a consistent basis, additional educational material may be delivered to emphasize the need for good nutrition. In some cases, a visit by a medical professional (virtual or in-person) may be needed to evaluate the patient's condition, particularly in the event that the received information indicates a potentially harmful medical condition. In some cases, block 812 may automatically set an appointment with a medical professional for the patient.

The subject matter described herein may be embodied in systems, apparati, methods, and/or articles depending on the desired configuration. In particular, various implementations of the subject matter described herein may be realized in digital electronic circuitry, integrated circuitry, specially designed application specific integrated circuits (ASICs), computer hardware, firmware, software, and/or combinations thereof. These various implementations may include implementation in one or more computer programs that may be executable and/or interpretable on a programmable system including at least one programmable processor, which may be special or general purpose, coupled to receive data and instructions from, and to transmit data and instructions to, a storage system, and at least one peripheral device.

These computer programs, which may also be referred to as programs, software, applications, software applications, components, or code, may include machine instructions for a programmable processor, and may be implemented in a high-level procedural and/or object-oriented programming language, and/or in assembly machine language. As used herein, the term "non-transitory computer-readable medium" refers to any computer program, product, apparatus, and/or device, such as magnetic discs, optical disks, memory, and Programmable Logic Devices (PLDs), used to provide machine instructions and/or data to a programmable processor, including a non-transitory computer-readable medium that receives machine instructions as a computer-readable signal. The term "computer-readable signal" refers to any signal used to provide machine instructions and/or data to a programmable processor. To provide for interaction with a user, the subject matter described herein may be implemented on a computer having a display device, such as a cathode ray tube (CRD), liquid crystal display (LCD), light emitting display (LED) monitor for displaying information to the user and a keyboard and a pointing device, such as a mouse or a trackball, by which the user may provide input to the computer. Displays may include, but are not limited to, visual, auditory, cutaneous, kinesthetic, olfactory, and gustatory displays, or any combination thereof.

Other kinds of devices may be used to facilitate interaction with a user as well. For instance, feedback provided to the user may be any form of sensory feedback, such as visual feedback, auditory feedback, or tactile feedback; and input from the user may be received in any form including, but not limited to, acoustic, speech, or tactile input. The subject matter described herein may be implemented in a computing system that includes a back-end component, such as a data server, or that includes a middleware component, such as an application server, or that includes a front-end component, such as a client computer having a graphical user interface or a Web browser through which a user may interact with the system described herein, or any combination of such back-end, middleware, or front-end components. The components of the system may be interconnected by any form or medium of digital data communication, such as a communication network. Examples of communication networks may include, but are not limited to, a local area network ("LAN"), a wide area network ("WAN"), metropolitan area networks ("MAN"), and the internet.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For instance, the implementations described above can be directed to various combinations and subcombinations of the disclosed features and/or combinations and subcombinations of several further features disclosed above. In addition, the logic flow depicted in the accompanying figures and/or described herein do not necessarily require the particular order shown, or sequential order, to achieve desirable results. It will be readily understood to those skilled in the art that various other changes in the details, devices, and arrangements of the parts and method stages which have been described and illustrated in order to explain the nature of this inventive subject matter can be made without departing from the principles and scope of the inventive subject matter.

What is claimed is:

1. A system for cooking prepared meals and determining compliance with a meal plan comprising:
an oven comprising a heating body, heating element, and at least one sensor,
wherein said oven is configured to cook a prepared meal having a meal code within an internal cavity of said heating body,
wherein said heating element is configured to heat said internal cavity of said heating body,
wherein said at least one sensor measures temperature data within said internal cavity of said heating body,
a control board operably connected to said at least one sensor and said heating element,
wherein said control board is configured to regulate an amount of power transferred to said heating element,
wherein said control board is configured to receive said temperature data from said at least one sensor,
wherein said meal code of said prepared meal is associated with cooking instructions that instruct said control board as to how to manipulate said heating element,
wherein said control board creates patient data based on said meal code of said prepared meal, a computing device operably connected to said control board,
   wherein said computing device is configured to receive patient data from said control board,
   wherein said patient data is used to determine compliance with a meal plan of a patient,
a processor operably connected to said control board and said computing device, and
a non-transitory computer-readable medium coupled to said processor,
   wherein said non-transitory computer-readable medium contains instructions stored thereon, which, when executed by said processor, cause said processor to perform operations comprising:
      creating patient data pertaining to a meal plan of said patient based on said meal code of said prepared meal,
      determining a degree of compliance for said patient with respect to said meal plan,
         wherein said degree of compliance is determined using said patient data and said meal plan,
         wherein said degree of compliance indicates whether said patient is conforming to said meal plan, and
      revising said meal plan in accordance with said degree of compliance.

2. The system of claim 1, further comprising additional instructions stored on said non-transitory computer-readable medium, which, when executed by said processor, cause said processor to perform additional operations comprising:
   receiving said meal code from a scanning device operably connected to at least one of said computing device or said control board,
   accessing cooking instructions associated with said meal code, and
   starting a preparation process based on said cooking instructions.

3. The system of claim 2, wherein said oven further comprises an output device, wherein said output device is configured to emit an audible instruction that informs said patient to perform a manual action that assists said control board to prepare said prepared meal.

4. The system of claim 3, further comprising additional instructions stored on said non-transitory computer-readable medium, which, when executed by said processor, cause said processor to perform additional operations comprising:
   pausing a preparation process based on cooking instructions,
   outputting an instruction that causes said output device to alerts said patient to perform a manual action, and
   restarting said preparation process after said manual action is performed by said patient.

5. The system of claim 1, further comprising a scanning device operably connected to at least one of said control board or said computing device,
   wherein said scanning device is configured to scan said meal code of said prepared meal and transmit said meal code thereto.

6. The system of claim 1, wherein said meal code further comprises meal data, wherein said meal data is saved as patient data within a user profile.

7. The system of claim 1, further comprising a database having a plurality of patient profiles stored therein,
   wherein said plurality of patient profiles contain user data of said patient, meal plan data, and said patient data,
   wherein said patient data comprises electronic health records of said patient and said degree of compliance with said meal plan.

8. The system of claim 1, further comprising:
   a display operably connected to at least one of said oven or said computing device, and
   a first user interface configured to allow said patient to input a palatability score for said prepared meal,
   wherein said first user interface presents said degree of compliance to said patient via said display.

9. The system of claim 8, further comprising a second computing device operably connected to at least one of said computing device or said control board,
   wherein said second computing device is configured to receive said degree of compliance for a plurality of user profiles,
   wherein a second user interface of said second computing device and said first user interface are configured to allow for communication therebetween when said degree of compliance has dropped below a lower limit of a compliance threshold.

10. The system of claim 9, further comprising additional instructions stored on said non-transitory computer-readable medium, which, when executed by said processor, cause said processor to perform additional operations comprising:
   comparing said degree of compliance to said lower limit to determine if said patient is not in compliance with said meal plan, and
   sending an instruction to said second computing device when said patient is not in compliance with said meal plan,
      wherein said instruction commands said second computing device to alert a medical professional that said patient is not in compliance with said meal plan.

11. A system for cooking prepared meals and determining compliance with a meal plan comprising:
   an oven comprising a heating body, heating element, at least one sensor, and camera,
      wherein said oven is configured to cook a prepared meal having a meal code within an internal cavity of said heating body,
      wherein said heating element is configured to heat said internal cavity of said heating body,
      wherein said at least one sensor measures temperature data within said internal cavity of said heating body,
      wherein said camera is configured to scan said meal code of said prepared meal,
   a control board operably connected to said heating element, at least one sensor, and camera,
      wherein said control board is configured to regulate an amount of power transferred to said heating element,
      wherein said control board is configured to receive said temperature data from said at least one sensor,
      wherein said control board is configured to obtain said meal code from said camera,
      wherein said meal code of said prepared meal is associated with cooking instructions that instruct said control board as to how to manipulate said heating element,
      wherein said control board creates patient data based on said meal code of said prepared meal,
   a database having a plurality of patient profiles stored therein,
      wherein said plurality of patient profiles contain said patient data, wherein said patient data comprises a electronic health records of a patient, meal data, and a degree of compliance, a processor operably connected to said control board and a computing device, and a non-transitory computer-readable medium coupled to said processor, wherein said non-transitory computer-readable medium contains instructions stored thereon, which, when executed by said processor, cause said processor to perform operations comprising:

creating patient data pertaining to a meal plan of said patient based on said meal code of said prepared meal, determining a degree of compliance for said patient with respect to said meal plan, wherein said degree of compliance is determined using said patient data and said meal plan, wherein said degree of compliance indicates whether said patient is conforming to said meal plan, and revising said meal plan in accordance with said degree of compliance.

12. The system of claim 11, further comprising additional instructions stored on said non-transitory computer-readable medium, which, when executed by said processor, cause said processor to perform additional operations comprising:

receiving said meal code from a scanning device operably connected to at least one of said computing device or said control board, accessing cooking instructions associated with said meal code, and starting a preparation process based on said cooking instructions.

13. The system of claim 12, wherein said oven further comprises an output device, wherein said output device is configured to emit an audible instruction that informs said patient to perform a manual action that assists said control board to prepare said prepared meal.

14. The system of claim 13, further comprising additional instructions stored on said non-transitory computer-readable medium, which, when executed by said processor, cause said processor to perform additional operations comprising:

pausing said preparation process based on said cooking instructions, outputting an instruction that causes said output device to alert said patient to perform said manual action, and restarting said preparation process after said manual action is performed by said patient.

15. The system of claim 11, further comprising a second computing device operably connected to at least one of said computing device or said control board, wherein said second computing device is configured to receive said degree of compliance for a plurality of user profiles, wherein a second user interface of said second computing device and a first user interface of at least one of said control board or said computing device are configured to allow for communication therebetween when said degree of compliance has dropped below a lower limit of a compliance threshold.

16. The system of claim 15, further comprising additional instructions stored on said non-transitory computer-readable medium, which, when executed by said processor, cause said processor to perform additional operations comprising:

comparing said degree of compliance to said lower limit to determine if said patient is not in compliance with said meal plan, and sending an instruction to said second computing device when said patient is not in compliance with said meal plan, wherein said instruction commands said second computing device to alert a medical professional that said patient is not in compliance with said meal plan.

17. A method of cooking a prepared meals and determining compliance with a meal plan comprising steps of:

obtaining an oven operably connected to a control board and comprising a heating body, heating element, and at least one sensor, wherein said oven is configured to cook a prepared meal having a meal code within an internal cavity of said heating body, wherein said control board is configured to regulate an amount of power transferred to said heating element in order to control a temperature within said internal cavity, wherein said control board is configured to receive temperature data pertaining to said temperature of said internal cavity from said at least one sensor, wherein said meal code of said prepared meal is associated with cooking instructions that instruct said control board as to how to manipulate said heating element, wherein said control board creates patient data based on said meal code of said prepared meal, scanning said meal code with a scanning device that is operably connected to at least one of said control board or a computing device operably connected to said control board, inserting said prepared meal into said oven, performing a manual action when prompted by said oven, wherein said control board is configured to send an instruction to at least one of an output device or said computing device when said cooking instructions require said manual action by a patient, wherein said instruction causes at least one of said output device or said computing device to alert said patient that said manual action must be taken, wherein at least one of said control board or said computing device determines said meal plan for said patient based on patient data and user data of said patient, wherein at least one of said control board or said computing device determines a degree of compliance for said patient, wherein said degree of compliance is determined using patient data and said meal plan, wherein said degree of compliance is used to revise said meal plan, inputting a palatability score into a user interface presented on a display of at least one of said oven or said computing device.

18. The method of claim 17, wherein said meal plan includes at least one dietary requirement and at least one dietary restriction.

19. The method of claim 17, wherein said control board is configured to transmit patient data to a meal preparation service, wherein said patient data instructs said meal preparation service as to which said prepared meal of a plurality of prepared meals to make for said patient.

20. The method of claim 17, wherein said meal plan is further revised using said palatability score.

\* \* \* \* \*